United States Patent [19]

Warnow et al.

[11] 4,227,519
[45] Oct. 14, 1980

[54] RESPIRATOR FOR EMERGENCY AIR SUPPLY TO A PATIENT

[75] Inventors: Detlef Warnow, Gross Grönau; Hans-Jörg Ziebrecht, Lübeck, both of Fed. Rep. of Germany

[73] Assignee: Drägerwerk Aktiengesellschaft, Fed. Rep. of Germany

[21] Appl. No.: 931,125

[22] Filed: Aug. 4, 1978

[30] Foreign Application Priority Data

Aug. 6, 1977 [DE] Fed. Rep. of Germany ....... 2735555

[51] Int. Cl.$^2$ ............................................... A62B 7/00
[52] U.S. Cl. ............................................... 128/205.24
[58] Field of Search ............... 128/145.8, 145.6, 145.5, 128/188

[56] References Cited

U.S. PATENT DOCUMENTS

| 3,754,550 | 8/1973 | Kipling | 128/145.8 |
| 3,910,270 | 10/1975 | Stewart | 128/145.8 |
| 4,057,059 | 11/1977 | Reid, Jr. et al. | 128/145.8 |

FOREIGN PATENT DOCUMENTS 2045494  3/1971  Fed. Rep. of Germany ........ 128/145.8

Primary Examiner—Robert W. Michell
Assistant Examiner—Thomas Wallen
Attorney, Agent, or Firm—McGlew and Tuttle

[57] ABSTRACT

A respirator for emergency supply to a patient, includes a respiratory gas supply which is connected through two control valves and two regulating valves to a patient. The regulating valves are coupled together by adjusting means which permits their adjustment and one is connected in the gas supply line to the first regulating valve, and the other is connected in the connection from the second regulating valve to the patient. The inhalation and exhalation time of the patient may be adjusted. The valve controls provide a time control which includes a control of the second regulator valve by two separate respirator gas volume connections of predetermined volume amounts which act on the second control valve to shift it into one of two defined positions. The second control valve establishes a respiratory gas connection in the inhaling phase through the second regulating valve and a ventilating valve which is connected directly to the patient.

4 Claims, 1 Drawing Figure

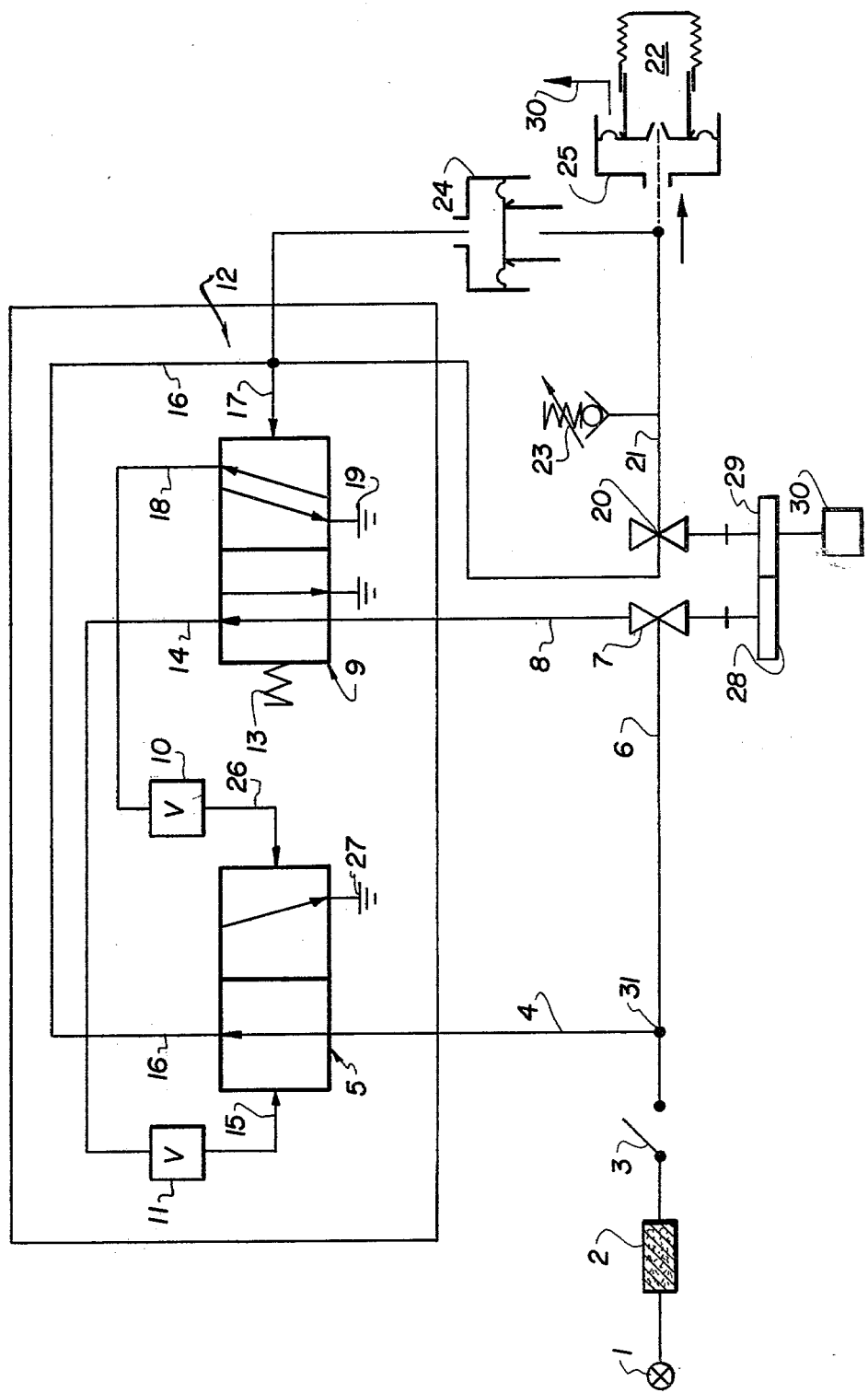

RESPIRATOR FOR EMERGENCY AIR SUPPLY TO A PATIENT

FIELD AND BACKGROUND OF THE INVENTION

This invention relates to respirators in general and, in particular, to a new and useful respirator, particularly for emergency supply, which includes a controlled time arrangement for varying the respiratory inhalation and exhalation time phases.

DESCRIPTION OF THE PRIOR ART

The subject of the invention is a simple respirator with which a patient may be safely ventilated, even by a layman, if necessary. It is independent of an additional energy supply and, to this end, the respiratory gas must be available as a supply under pressure in the portable, and thus lightweight, small size respirator.

A known respirator, particularly suitable as a portable device, consists of pneumatic elements. The supply of the respiratory gas which maintains the breathing of the patient is effected over a pipe line system to an opening leading to the patient and to a control valve which has an outlet opening for the respiratory gas into the atmosphere. The control valve has a control chamber with which the delivery of the respiratory gas from the outlet opening is regulated and with which corresponding inhalation and exhalation conditions can be provided in the line leading to the patient.

The ratios of inhalation to exhalation time can be varied to permit adaptation to different requirements. The device permits a volume-limited operation where a constant gas volume is fed to the patient, as well as a pressure-limited operation. In any case, the respiratory gas is conducted continuously to the patient.

A disadvantage of this construction is the relative complicated design of the apparatus which results in a great number of structural elements with their dimensions and weights, and the complicated pneumatic control is difficult to handle. The greatest difficulty, however, is the great consumption of respiratory gas. In addition, a portable device should be lightweight and consumption should only be used for direct respiration. The continuous flow of the respiratory gas determines the high consumption, see German DOS No. 25 25 359.

A control in a respirator is known which permits automatic auxiliary and controlled respiration of patients by using pneumatic structural elements. The control is effected from a control chamber to which the respiratory gas supply and the patient line are connected over an injector. Respiratory gas is supplied to the pressure chamber for conveyance to the patient by an inspiration trigger and an expiration trigger, which are pressure-controlled. To this end, the feed cock is opened by underpressure in the inhalation phase which closes again after the normal pressure has been restored.

Pressure-controlled devices cannot be used for many cases of first aid respiration, since they do not supply a constant respiration volume to the patient. The patient produces a frequently varying counterpressure due to the varying secretion of the respiratory tract, compared to the respiratory gas to be supplied. In a pressure-controlled respirator, this leads to different respiration volumes in the alveoloar pulmonary region. (See German DOS No. 19 51 637).

SUMMARY OF THE INVENTION

The present invention provides a respiratory device for emergency supply in acute cases with a pneumatic control, while still maintaining satisfactory physiological respiration parameters with regard to the respiration frequency, the respiration volume and the respiration time ratio.

The present invention makes it possible, with a few proven structural elements, to obtain a small and reliable respirator for emergency supply. The preselected constant respiration time ratio of 1:1.5, which is a favorable value for both children and adults for emergency supply outside of the clinic, permits adaptation of the breathing with satisfactory physiological respiration to the respective patient simply by free selection of the respiration frequency and of the respective respiration volume. The pressurized respiratory gas supply contained in the respirator performs all control and switching functions automatically in a simple manner. The respiration frequency and the respiration volume can thus be adjusted as desired.

An embodiment of the invention where the flow valve and regulating valve are interconnected by coupling elements, including an adjusting device, permits a single knob operation of the respirator by a corresponding design of the coupling elements, utilizing the known respiration frequency values and the respective respiration volume for infants, children and adults. In this way, the apparatus can also be used for acute emergencies by medical layman. It can then be adjusted to the patient by an adjusting device. Respiration errors by false adjustment are practically impossible.

Accordingly, it is an object of the invention to provide an improved respirator device having first and second regulating and first and second control valves connected so that the controlled time for inhalation and exhalation of the patient may be effected in accordance with the coupling of the regulating valves and the operation of the control valves under the influence of predetermined volumes of respirator gas.

A further object of the invention is to provide a respirator device which is simple in design, rugged in construction and economical to manufacture.

The various features of novelty which characterize the invention are pointed out with particularity in the claims annexed to and forming a part of this disclosure. For a better understanding of the invention, its operating advantages and specific objects attained by its uses, reference is made to the accompanying drawing and descriptive matter in which a preferred embodiment of the invention is illustrated.

BRIEF DESCRIPTION OF THE DRAWING

The only FIGURE of the drawing is a schematic view of a respirator system constructed in accordance with the invention.

DESCRIPTION OF THE PREFERRED EMBODIMENT

Referring to the drawing in particular, the invention embodied therein, comprises, a respirator gas supply system for a patient which is shown in the drawing by a schematic connection piece 22 for the patient. The respiratory gas flows from the respiratory gas supply 1, which is under pressure, over filter 2, main switch 3, through line or first portion 4 to the second control valve 5, which is designed for a 3/2 function.

At 31, a second portion or line 6 is connected to the first portion or line 4, which extends over regulating valve 7 as line 8 to the first control valve 9 which has a 5/2 function. The two control valves 5 and 9 together, form with the second volume 10 and the first volume 11, a time control unit, generally designated 12. The two control valves 5 and 9 are equipped with a mechanical delay mechanism so that they switch only when a certain switching pressure is attained. Due to spring 13, the first control valve 9 is a monostable switching element with preferential control of line 8 after control of line 14, with which the second control valve 5 is controlled over the first volume 11.

During a time constant, referred to herein as $T_1$, which results from a pneumatic resistance R of regulating valve 7 and capacitance $C_{11}$ of the first volume 11, the second control valve 5 is controlled at 15 with a continuous pressure rise. When the switching pressure has been attained, line 4 connects through to a respiratory discharge line 16, and the second control valve 5 then remains stable in this through-connected state. The pressure from line 4 over line 16 then reaches a pressure control 17 of the first control valve 9 and, at this point, switches line 8 to control line 18. At the same time, control line 14 is released over vent 19. The respiratory gas flows over line 16 through flow valve 20 and through line 21 to the user, represented as a connection to a patient 22. At the end of the time constant $T_1$, inhalation is started. A pressure-limiting valve 23 and valve 24, ventilating in the exhalation phase, are connected to a line 21. Respiration valve 25 which is connected ahead of patient 22 permits the flow of the respiratory gas and controls the exhalation of the patient into the atmosphere via a discharge 30.

Upon switching of line 8 to line 18 by the first valve 9, the time constant $T_1$ is started, which determines the inhalation time. The second control valve 5 is then connected to the control line 18 and the second volume 10 and line 26. After the switching pressure has been attained in line 26, the passage from line 4 to line 16 is blocked by the switching of the second control valve 5 and, with the end of the time constant $T_1$, the inhalation is also ended. Time constant $T_2$ results from the pneumatic resistance R of regulating valve 7 and capacitance designated $C_{10}$ of the second volume 10. With the end of time constant $T_2$ and the new start of time constant $T_1$, respiratory gas no longer flows to the patient 22, so that the valve 25 becomes pressureless and ventilates line 21. The patient 22 can exhale over respiration valve 25. With the ventilation of line 16, control line 17 for the first control valve 9 becomes pressureless, and line 8 is again steered to control line 14 by spring 13. Thus, time constant $T_1$ always runs with the start of the pressure rise in the second control valve 5.

Time constant $T_1 = R \times C_{11}$ and it determines the length of the exhalation time, and time constant $T_2 = R \times C_{10}$, and it determines the length of the inhalation time. The respiration time ratio is $$\frac{T_2}{T_1} = 1 \times \frac{C_{10}}{C_{11}}$$

By a certain selection of the two pneumatic volumes 10 and 11, the respiration time ratio $T_2/T_1$ is determined as a constant.

The respiration frequency results with $C_{11} + C_{10} = K$ as $$f = \frac{1}{T_1 + T_2} = \frac{1}{R(C_{11} + C_{10})} = \frac{1}{R(K)}$$

as a function of the pneumatic resistance R varying with regulating valve 7.

The respiration time ratio $$\frac{T_2}{T_1} = \frac{1}{1.5},$$

fixed by the corresponding selected two volumes 10 and 11, permits the determination of associated values of respiration frequency and respiration volume for the emergency supply of acutely ill patients outside the clinic to maintain the vital functions for infants, children and adults alike. The following correlations are obtained:

For adults: respiration frequency 15/min. respiration volume 700 cc.

For children: respiration frequency 30/min. respiration volume 200 cc.

Regulating valve 7 regulates the respiration frequency, flow valve 20 regulates the respiration volume. Regulating valve 7 and flow valve 20 are connected with each other over coupling elements 28 and 29. Regulating valve 7 and flow valve 20 are both adjusted by rotating adjusting device 30. By a corresponding design of coupling elements 28 and 29, the corresponding correlations respiration frequency-respiration volume are automatically set by operating adjusting device 30.

While a specific embodiment of the invention has been shown and described in detail to illustrate the application of the principles of the invention, it will be understood that the invention may be embodied otherwise without departing from such principles.

What is claimed is:

1. A respiratory gas supply system for a patient, comprising, a respiratory gas supply, first and second control valves, a first pressure line connected to said second control valve for influencing the regulation of the control position of said second control valve, a second pressure line connected from said first control valve to said second control valve for influencing the regulating position of said second control valve, a respiratory gas supply line having a first portion connected to said second control valve and a second portion connected from said first portion to said first control valve, a first regulating valve in said second portion, a respiratory discharge line connected from said second control valve to the patient, a second regulating valve in said respiratory discharge line, a first gas volume container of a predetermined volume in said first pressure line, a second gas volume container of a predetermined volume in said second pressure line, adjustable coupling means coupling said first regulating valve and said second regulating valve, spring means acting on said first control valve to influence the regulating position of said first control valve, a pressure control counteracting said spring means connected from said respiratory discharge line to said first control valve for also influencing the regulation of said first control valve, whereby, during an exhalation time $T_1$, said second control valve being controlled by said first pressure line to produce a continuous pressure rise from the resistance of said first regulating valve in said first volume up to a switching pressure of said second control valve to effect the subsequent movement of said second control valve to connect said respiratory air discharge line to said first portion of said respiratory gas supply line, said respiratory gas discharge line providing pressure to actuate said first control valve to connect said second portion to said second pressure line so that respiratory gas flows through said respiratory discharge line to the patient for inhalation, and when inhalation ends, thereby permitting the patient to exhale so that said first control valve is connected to said second pressure line and said second control valve is shifted to interrupt the connection of said supply line first portion to said discharge line to end inhalation, the beginning of exhalation being initiated by the resistance of said first regulating valve and the amount of said first volume, said spring means acting on said first control valve to provide a pressure to activate said second control valve.

2. A pneumatically controlled respirator for emergency supply of air to a patient with which an amount of respiratory gas set by a regulating valve (20) is fed to the patient from a respiratory gas supply, and wherein the inhalation and exhalation times ($T_1$, $T_2$) are adjustable, comprising a time control unit (12) having a first control valve (20), a first connection (6, 8) between said first control valve and the respiratory gas supply, a resistance regulating valve (7) in said first connection, a second control valve (5), a first control line (14) having a first defined volume (11) and a second control line (18) with a second control volume (10) each connected between said first valve and control connections (15-26) of said second control valve acting on said second control valve to urge it into respective opposite end positions, a discharge line (4, 16, 21) connected over said second-control valve and connectable to the patient, said second control valve providing a regulation of said discharge line to the patient, a ventilation valve (25) connectable to the patient and connected to the discharge line from said second control valve, said second control valve being moved into a position interrupting flow in said discharge line to permit exhalation of the patient after said inhalation time which corresponds to the filling of said second volume from said first connection through said first control valve, a second connection (17) between said discharge line and said first control valve for moving said first control valve into a position connecting said first connection to said second control line, and spring means connected to said first control valve for moving said first control valve into a position connecting said first connection to said first control line when said second control valve is moved to interrupt flow in said discharge line.

3. A pneumatically controlled respirator, as claimed in claim 2, wherein the breathing time ratio is represented by:

$$\frac{T_2}{T_1} = \frac{\text{2nd volume (10)}}{\text{1st volume (11)}} = \frac{1}{1.5}$$

4. A pneumatically controlled respirator, as claimed in claim 2, wherein said regulating valve and said flow valve are connected with each other by coupling elements having a common adjusting device.

* * * * *